United States Patent [19]

Doyle

[11] Patent Number: 5,773,825
[45] Date of Patent: Jun. 30, 1998

[54] BI-LAYER ATTENUATED TOTAL REFLECTANCE DEVICE PROVIDING OPTIMIZED ABSORBANCE LINEARITY

[75] Inventor: Walter M. Doyle, Laguna Beach, Calif.

[73] Assignee: Axiom Analytical, Inc., Irvine, Calif.

[21] Appl. No.: 697,439

[22] Filed: Aug. 23, 1996

Related U.S. Application Data

[63] Continuation-in-part of Ser. No. 532,164, Sep. 22, 1995, abandoned.

[51] Int. Cl.⁶ ................................................. G01N 21/01
[52] U.S. Cl. .............................. 250/339.11; 250/339.12; 250/341.2
[58] Field of Search .................... 250/339.11, 339.12, 250/341.2, 341.8, 900; 356/244

[56] References Cited

FOREIGN PATENT DOCUMENTS

2228083  7/1990  United Kingdom ............. 250/339.11
9009574  8/1990  WIPO ............................... 250/339.11

Primary Examiner—Michael J. Tokar
Assistant Examiner—Richard Hanig
Attorney, Agent, or Firm—Thomas J. Plante

[57] ABSTRACT

A sensing apparatus for spectral analysis in which the sensing head is bi-layered. The layer contacting the sample is formed of corrosion-resistant material, e.g., diamond. It is engaged by a supporting layer formed of infrared transparent material, e.g., zinc selenide through which radiation passes on its way to and from the sample-contacting layer. In order to avoid non-linearity in the sample absorbance results, incoming paraxial rays are all reflected in such a way that they are reflected at the same angle, and the same number of times, from the sample contacting surface of the corrosion resistant layer. The incoming rays may be reflected at a conical surface, or at a flat rooftop-like surface. The exiting rays are preferably reflected so that they are parallel to the incoming rays. Where a conical reflecting surface is used, it may be a surface of the zinc selenide layer, or a highly reflective surface provided by another element. In order to insure that each ray is reflected the same number of times at the sample, certain relationships are maintained between the width dimension of the return reflection surface (i.e., the reflection surface which causes rays to return to the sample after a previous reflection) and the thickness dimension between the return reflection surface and the sample.

20 Claims, 9 Drawing Sheets

BI-LAYER ATTENUATED TOTAL REFLECTANCE DEVICE PROVIDING OPTIMIZED ABSORBANCE LINEARITY

This application is a continuation-in-part of application Ser. No. 532,164, filed Sep. 22, 1995 now abandoned.

BACKGROUND OF THE INVENTION

This invention relates to internal reflectance spectroscopy, and primarily to the construction of an attenuated total reflectance (ATR) device used to cause measurable absorbance of radiation by a sample.

Two patents relating to this field of development have been issued to assignees of the present inventor. U.S. Pat. No. 4,835,389 disclosed an IRE at the lower end of a single cylindrical hollow tube. Pat. No. 5,051,551, assigned to the assignee of this application, disclosed an immersion probe comprising a pair of hollow light pipes which conduct IR radiation to and from an ATR element which may or may not also serve as the retroreflecting element. Another application of the present inventor, assigned to the assignee of this application, Ser. No. 08/188,898, filed Jan. 31, 1994, related to a sensing head provided by a "conical-shaped piece of infrared (IR)—transparent material which serves both as an ATR element and as a retroreflector".

In an article in "Spectroscopy May 1995", Milosevic et al described an ATR probe having a bi-layer or "composite" ATR element, consisting of a thin flat layer of a chemically resistant material, such as diamond, sandwiched together with a thicker element composed of a less resistant, but infrared transparent material, such as zinc selenide (ZnSe). The two materials are in optical contact, so that IR radiation can pass from one to the other without being reflected. The outer surface of the larger element is shaped so as to serve as a curved reflector which focuses the IR radiation into the thin, chemically resistant layer.

The referenced article does not provide a detailed description of the Milosevic ATR element. However, it does state that "reflecting radiation forms a focal semi-ring at the entrance aperture of the diamond disk." It is assumed that the geometry is something like that shown in FIG. 1 or FIG. 2 of this application.

Figure 1:
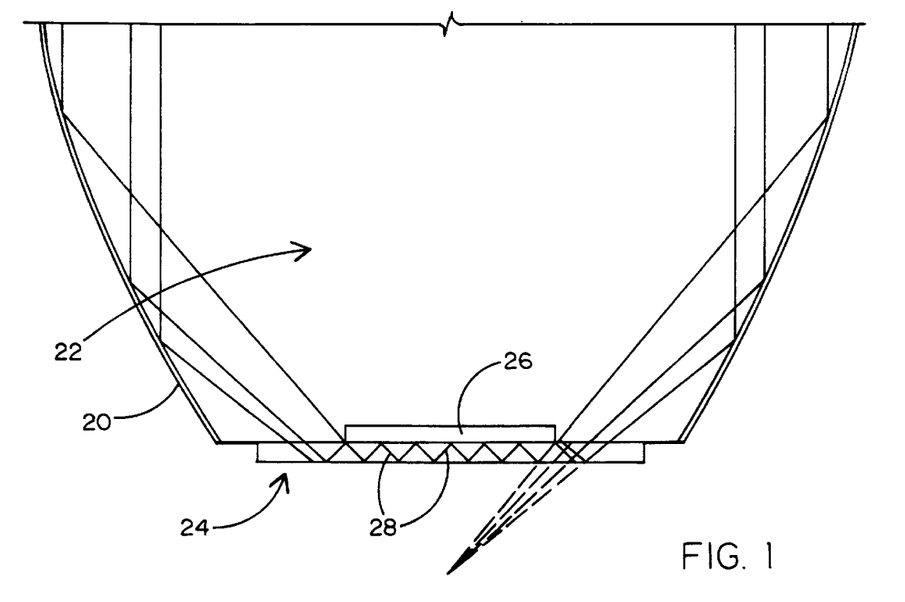
Figure 2:
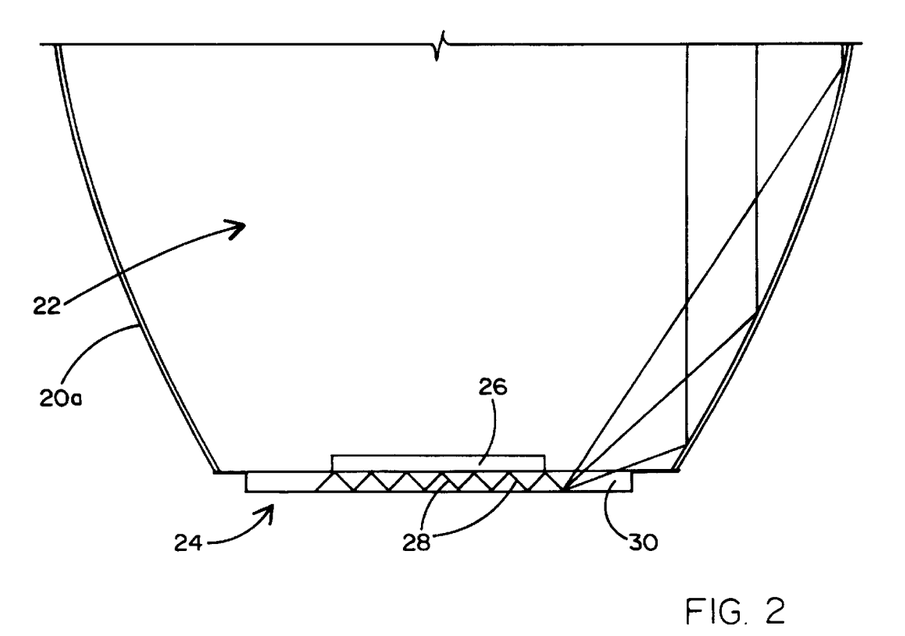
Figure 3:
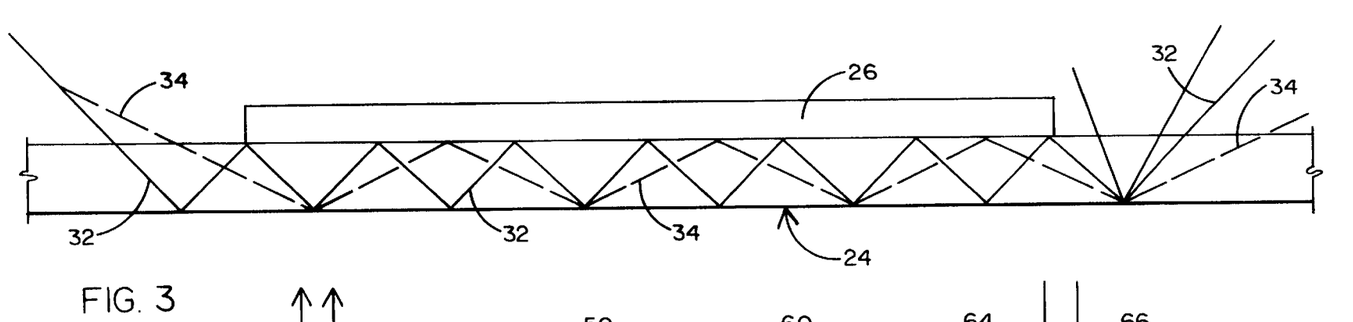
FIG. 3 illustrates the rays traveling in the sample-contacting element of FIGS. 1 and 2.

The designs illustrated by FIGS. 1 and 2 are defective because they suffer from severe non-linearity, thereby providing misleading spectral information regarding sample absorbance. This problem of non-linearity has been demonstrated by laboratory tests. FIG. 3 illustrates the non-linearity situation of the devices of FIGS. 1 and 2.

What is needed is an ATR probe design having a bilayer element which avoids the problem of non-linearity in spectral results. In ATR probes, there are two potential causes of non-linearity. One cause relates to the angles used for spectral analysis, i.e., the angles at which light rays are reflected at the sample surface. The other cause relates to the number of reflections of each ray at the sample surface.

Variations in the angle of incidence in an ATR device can affect the measured absorbance in two ways. First, the number of reflections in an ATR element of a given length and thickness is determined by the angle of incidence. Secondly, the optical penetration depth and hence effective sample thickness per reflection is dependent on this angle. An ATR device which uses a wide range of angles of incidence is thus analogous to a wedged transmission cell. But in this case, the wedge involves not only a gradual variation but also one or more discrete steps corresponding to the different numbers of reflections. The result is a complicated nonlinear dependence of absorbance on concentration. This is quite difficult to handle analytically. To minimize the impact of this effect, it is essential to restrict the distribution of incident angles to the minimum possible value. And it is especially important to make sure that this value is low enough so that all rays have the same number of reflections.

In the case of a partially absorbing ATR element (such as diamond between 1400 and 1800cm$^{-1}$), the situation is even more complicated. The element absorption will selectively attenuate those rays which have longer pathlengths through the element. These are the rays which have the lower angles of incidence and hence the greater penetration depth and number of reflections. The result will be lower values of measured absorbance for spectral bands in such regions compared to bands in regions where the element does not absorb.

SUMMARY OF THE INVENTION

The present invention discloses a structure having the benefits of the damage resistant sample-contacting layer (such as a diamond or cubic zirconia element) combined with a ray reflection pattern at the sample which is not subject to the deficiency of non-linearity in spectroscopic test results.

The present invention provides a bi-layered ATR device using a radiation-directing and reflecting structure which solves both of the non-linearity problems discussed above. It insures that all sample-penetrating rays will be reflected at substantially the same angle by the sample contacting surface. It also insures that the number of reflections of each ray at the sample is equal to the number of such reflections of the other rays.

The requirement for same angle reflectance is met by causing all rays entering the ATR sample-contacting element to be parallel to one another, except for unavoidable divergence of up to 2°. The rays entering the probe are paraxial. They are reflected into the ATR element by a straight line inclined surface, such as a wedge-shaped or, preferably, conical surface, so that each ray has substantially the same angle of incidence at the sample.

The requirement for equal number of sample reflections for each ray depends on certain dimensional relationships in the ATR design. The relevant dimensions are linear: (a) the width of the space through which each light ray enters the ATR and (b) the thickness of the ATR within which each light ray is reflected back and forth before it exits from the ATR.

BRIEF DESCRIPTION OF THE DRAWINGS

FIGS. 1–3 show the prior art concept having a bi-layered sensoror ATR spectroscopy. FIGS. 1 and 2 are sectional views, showing slightly different versions of the device.

FIGS. 12 and 13 illustrate schematically two possible conditions if the required dimensional relationship is not adhered to;

DETAILED DESCRIPTION OF SPECIFIC STRUCTURES

FIGS. 1 and 2 show prior art structures. In FIG. 1, the axially symmetric surface 20 of a ZnSe element 22 is assumed to be parabolic. Radiation traveling parallel to the axis will enter the rear surface of this element and be reflected by the parabolic surface toward the focal point of the parabola. However, the lower end of the parabola is truncated and capped with a flat diamond element 24. Thus, before it can reach the focus, a portion of the radiation enters the diamond element, where it is reflected several times, as shown. After several reflections, it emerges from the diamond element 24 and is reflected back in an axial direction by the parabolic ZnSe surface. A circular recess 26 in the lower surface of element 22 causes rays 28 inside the diamond element 24 to be reflected by the upper surface of the diamond element.

FIG. 2 is similar to FIG. 1, except that the axially symmetric surface 20a is modified from the parabolic shape in order to bring the light to focus in a ring at the aperture end 30 of the diamond element 24. This will maximize the amount of radiation getting into the diamond, but will also increase the angular divergence (range of ray angles) being used. This design seems to correspond to the description given in the article.

FIG. 3 illustrates the non-linearity problem inherent in the structures of FIGS. 1 and 2. FIG. 3 is an enlargement of the diamond element of FIG. 2, showing the paths taken by two of the rays after they enter the element. The third ray shown in FIG. 2 is actually reflected too sharply to remain in the diamond element. For this illustration, the two rays shown (32 and 34) have a factor of two difference in the number of reflections they make in the diamond element. In addition, the ray 34 with fewer reflections has a higher angle of incidence, so that the depth of penetration into the analyte for each reflection will be considerably less than that of ray 32. As a result, ray 34 will experience substantially less than half of the total absorbance of ray 32. This disparity will lead to quite significant nonlinearity.

Figure 4:
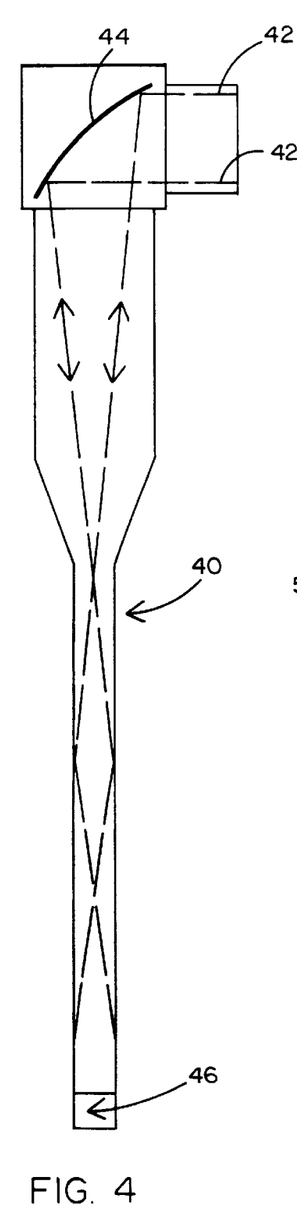
FIG. 4 is a schematic which shows a probe in which an ATR tip element may be used.

FIG. 4 shows schematically a probe which may be used to insert an ATR device into a reactor for in situ monitoring of sample material. The probe has an extended tubular body 40, typically 16 mm in diameter, which acts as a light-confining enclosure. Entering light is shown as a collimated beam 42, which is reflected by a parabolic mirror 44, causing the reflected light to have a soft focus, which approximates a collimated beam, i.e., having a beam spread of about 5°.

The inner surface of tube 40 is coated with highly reflective material which causes the maximum amount of radiation to travel in both directions within light pipe 40. The lower end of tube 40 has a tip assembly 46 which comprises an ATR sensing device.

Figure 5:
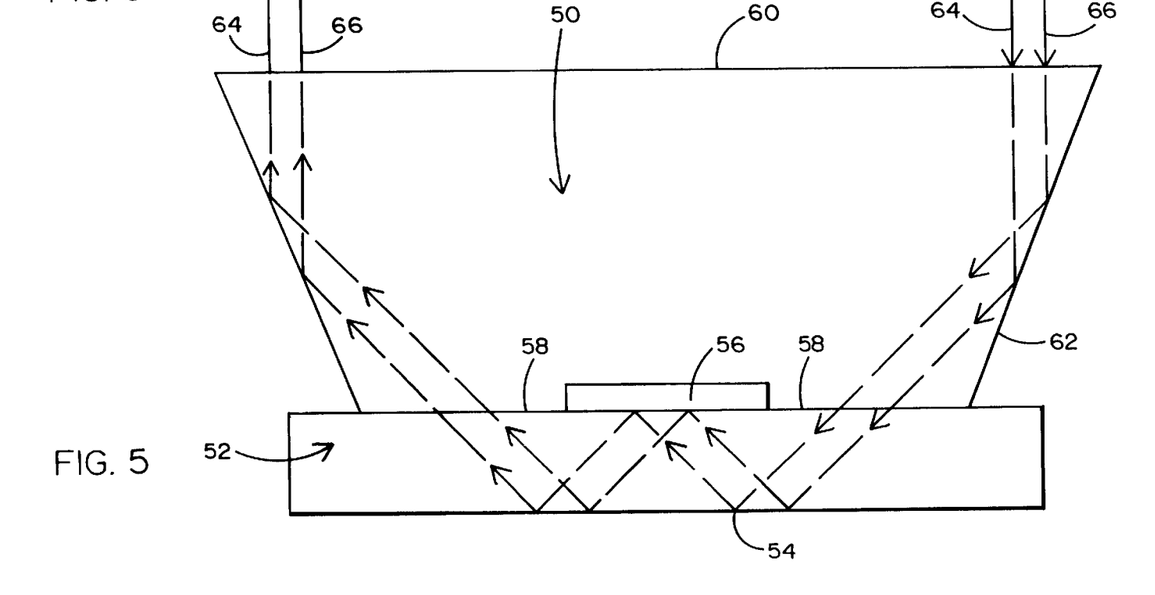
FIG. 5 is a schematic showing a bi-layered ATR sensor which is an embodiment of the present invention.

FIG. 5 is a cross-section showing an embodiment of the present invention, which essentially solves the non-linearity problem discussed above. As will be further explained below, various structural arrangements can avoid the non-linearity problem, provided certain dimensional relations are adhered to.

FIG. 5 shows a bi-layered ATR device having a relatively thick upper supporting element 50 and a lower sample-contacting element 52. Elements 50 and 52 are pressed together so that there is optical contact between them. The upper element 50 is a solid block of an infrared transparent material, such as zinc selenide (ZnSe). The lower element 52 is a layer of sample-resistant optical material, such as diamond. The element 50 is a relatively thick block, and the element 52 is a relatively thick plate, whose lower surface 54 is in contact with the sample material. A recess 56 in the lower surface of element 50 confines the optical contact between elements 50 and 52 to an annular area 58, through which the entering and exiting rays travel to and from the sample-contacting surface 54.

The incoming rays are not directed toward a focal point or focal ring, as they are in the structures of FIGS. 1–3. Instead, they are reflected off a linear, slanted surface on their way to the diamond layer 52. This insures that each of the paraxial rays will be reflected at the same angle when it reaches the sample-contacting surface 54 of layer 52.

Preferably, the reflecting surface of upper element 50 is conical, i.e., its overall shape is frusto-conical. This assumes that the horizontal cross-section of element 50 shows a round shape. Another option is to have a shape which is wedge-shaped in vertical cross-section, and rectangular in horizontal cross-section, in which entering and exiting rays are reflected by two flat slanted surfaces.

In FIG. 5, which is the currently preferred version of the present invention, the supporting element 50 has a rear surface 60 through which infrared rays enter and exit. The side wall 62 of element 50 is conical, with the result that all of the paraxial rays are so reflected that they make the same angle with the axis of the ATR device. When projected onto an axial plane, as shown in the figure, they are unfocused. Since all of the paraxial rays, after reflection into the diamond element 52, make the same angle with the vertical axis of the ATR device, all of them will strike the interface between the diamond element and the analyte (sample) at the same angle. This consistency of angle of incidence is one condition needed to ensure linearity of the absorbance measurements. The second condition needed to insure linearity of absorbance measurements is based on linear dimensional relations described with reference to FIGS. 11–13.

In FIG. 5, two rays are represented by dashed lines, rays 64 and 66. The illustrated rays 64 and 66 are parallel to the central axis of the ATR element. Such paraxial rays enter from all portions of the annular area 58. They are reflected off conical surface 62 at the same angle, and they enter diamond element 52 without reflection. Each ray is reflected at the same angle when it reaches sample contact surface 54. Also, each ray has the same number of reflections at surface 54, a result which is insured by the dimensional requirements illustrated in FIGS. 11–13.

In the illustrated embodiment, the number of such reflections of each ray is two. A design may be employed having a larger number of reflections. Limiting the number of reflections serves to maximize the effective aperture, i.e., the fraction of the cross-section which can be used for incident radiation. This is important in view of the fact that the radiation is not being focused into the element aperture. Experience has shown that a two reflection ATR device is adequate for most applications.

If desired, only one reflection of each ray may be used. For that purpose, obviously, no reflection back to the sample surface would occur. Each ray should be reflected at substantially the same angle from the sample surface.

As the number of sample surface reflections is increased, the non-linearity in data caused by a difference of one in the sample surface reflections becomes less critical. For example, an apparatus in which rays are reflected seven times or eight times would have less problems of non-linearity than the illustrated embodiments of the present invention. A "tunnel cell" IRE (internal reflectance element) of the type shown in common assignee U.S. Pat. No. 4,988,195 has numerous reflections of each ray at the sample surface, many more than the present type of ATR element.

In order to realize the desired optimal absorbance linearity in the present apparatus, certain dimensional conditions are required. These conditions pertain (1) to the size of the entering and exiting apertures for rays which are reflected by the sample, and (2) to the distance through which the rays travel between the surface of the sample and the surface which reflects sample-reflected rays back to the sample surface.

Figure 11:
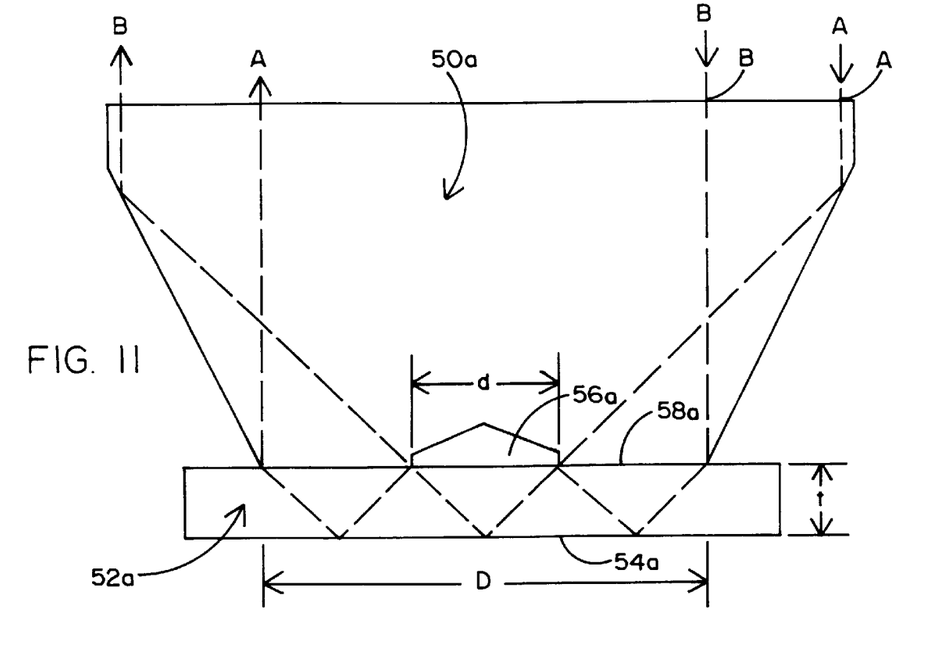
FIG. 11 is a schematic illustrating the dimensions whose relationship is significant in the preferred embodiment of FIG. 5.

FIG. 11 shows schematically the embodiment of FIG. 5, and identifies certain dimensions which need to have specified relationships to one another. In FIG. 11, the backing element is designated 50a and the sample-engaging element is designated 52a. The lower surface 54a of element 52a is in contact with the sample. The recess 56a in the lower surface of element 50a confines the optical contact between elements 50a and 52a to the annular area 58a.

The critical dimensions of the elements 50a and 52a are linear and are indicated by the letters "d", "D", and "t". The letter d represents the diameter of the recess 56a. The letter D represents the diameter of the circle formed where the reflecting surface 62a of element 50a engages the upper surface of element 52a, i.e., the periphery of the annular area 58a.

The letter t represents the linear distance between the two reflecting surfaces at which the rays are reflected back and forth as their absorbance by the sample is being measured. One reflecting surface is the sample surface 54a. In FIG. 11, the other reflecting surface is the portion of the surface of element 52a which is located at recess 56a. Dashed lines "A" and "B" represent the optical rays which enter the ATR element at the extreme outer and inner edges of its acceptance area. The critical dimensions have been set so that each of these rays (and any rays between them) experience exactly two reflections at the interface between the ATR element and the sample. It can be seen that, if the angle of incidence is set at 45 degrees, this condition occurs when the following conditions are met:

d=2t and D=3d

Figure 12:
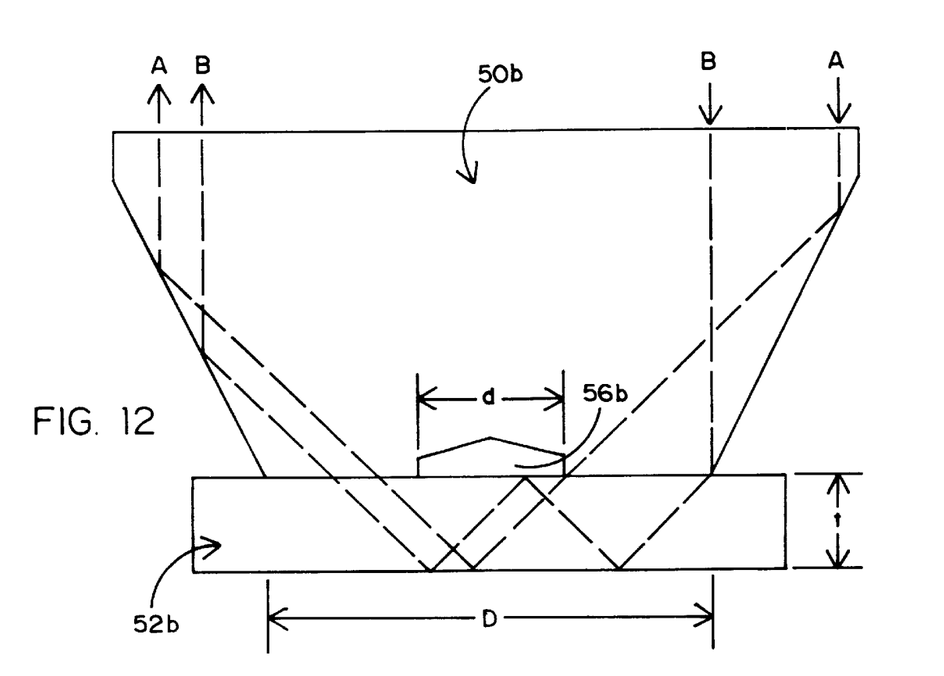
Figure 13:
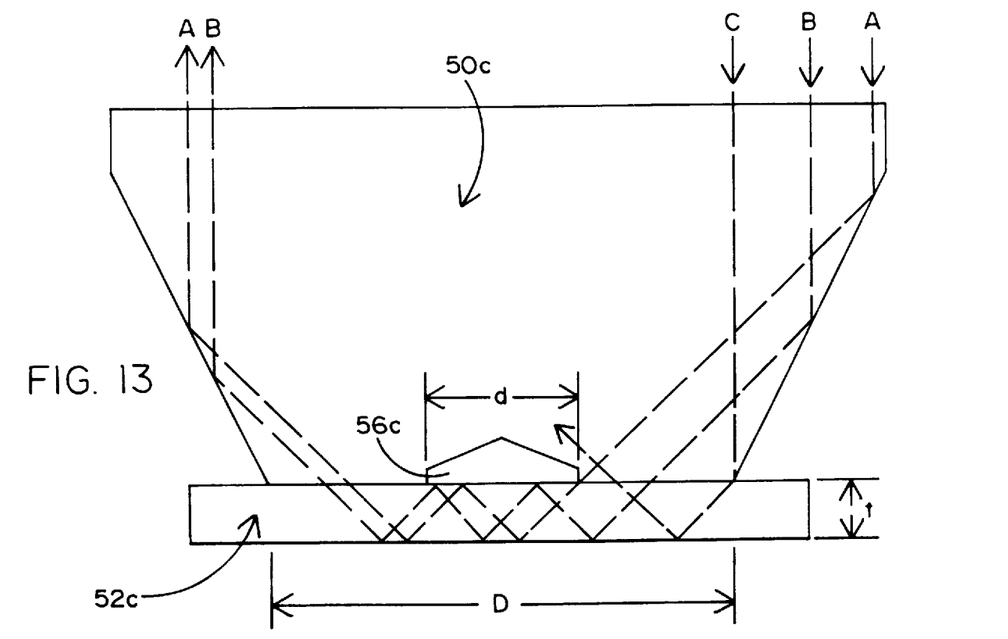

FIGS. 12 and 13 illustrate two possible conditions that would occur if the above requirement is not adhered to. In FIG. 12, the outer (sample contacting) element 52b is too thick, i.e., 2t>d. It can easily be seen that ray B experiences two reflections, while ray A experiences only one. This would give rise to an inherently nonlinear dependence of measured absorbance on concentration.

In FIG. 13, the outer element 52c is too thin, i.e., 2t<d. In this case, ray A experiences two reflections, while ray B experiences three, and ray C misses the air gap (recess 52c) and is thus lost. Again, this is a very undesirable condition.

Figure 6:
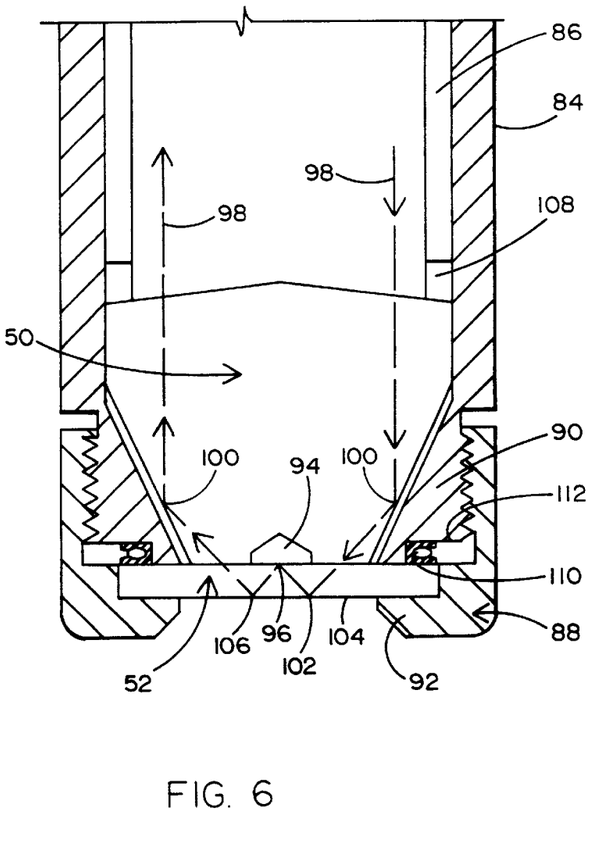
FIG. 6 is a cross-section showing the mechanical design of a probe utilizing the concept of FIG. 5.
Figure 7:
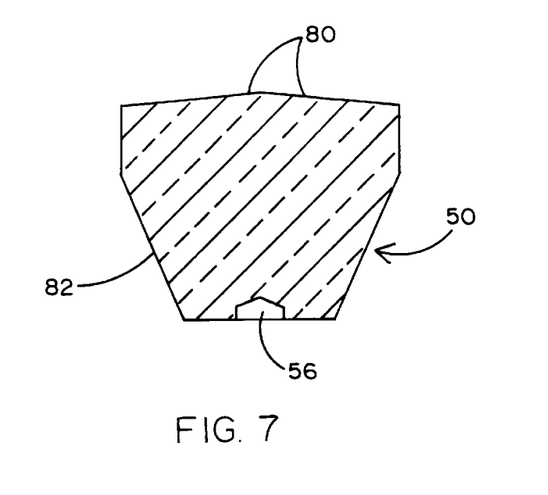
FIG. 7 is a section showing the construction of a preferred form of the infrared transparent element used in FIGS. 5 and 6.

FIG. 6 illustrates the mechanical design of a probe utilizing the concept of FIG. 5. The zinc selenide backing element 50 for this design is shown in FIG. 7. For this embodiment, the rear surface 80 of the backing element 50 is in the shape of a shallow cone (5 deg. from the normal to the axis). This provides the benefit of minimizing stray light, caused by back surface reflection. Since the shallow cone deviates the optical rays as they enter the backing element, the angle of the conical reflecting surface 82 of this element is adjusted to compensate for this. As a result, rays which are parallel to the axis before entering the backing element 50 will be traveling at 45° to the axis after reflection.

The mechanical design of the sensing element shown in FIG. 6 includes an outer tubular body (or shell) 84, inside which light pipe 86 is supported. The ATR device, which comprises supporting element 50 and diamond element 52, is held in place at the end of body 84 by a cylindrical cap 88 which is screwed onto the end of body 84. The lower end of body 84 has an extension 90, whose cylindrical outer surface is threaded to engage the inner threads on cap 88.

The diamond element 52 is engaged by an annular flange 92 on cap 88. Screwing cap 88 on outer body 84 causes the diamond element 52 to press tightly against the lower surface of the zinc selenide element 50. A gap 94 in the lower surface of element 50 causes the rays inside element 52 to have a centrally located reflection from the upper surface of element 52 at point 96.

A typical ray 98 is shown passing downward through element 50, being reflected off the conical wall 100 of element 50, then traveling into element 52, where it is reflected at point 102 on the sample contacting surface 104. After reflection at point 96, ray 98 is reflected for the second time at point 106 on the sample contacting surface 104. Thereafter, ray 98 is reflected again on conical wall 100, and passes upward along a path parallel to its downward path.

In order to provide resilient pressure on the elements of the ATR device, an annular compliant washer 108 is pressed between the upper edge of element 50 and the lower end of light pipe 86. Also a spring-loaded annular seal 110 is pressed between the upper surface of element 52 and the lower end 112 of extension 90 of body 84.

Figure 14:
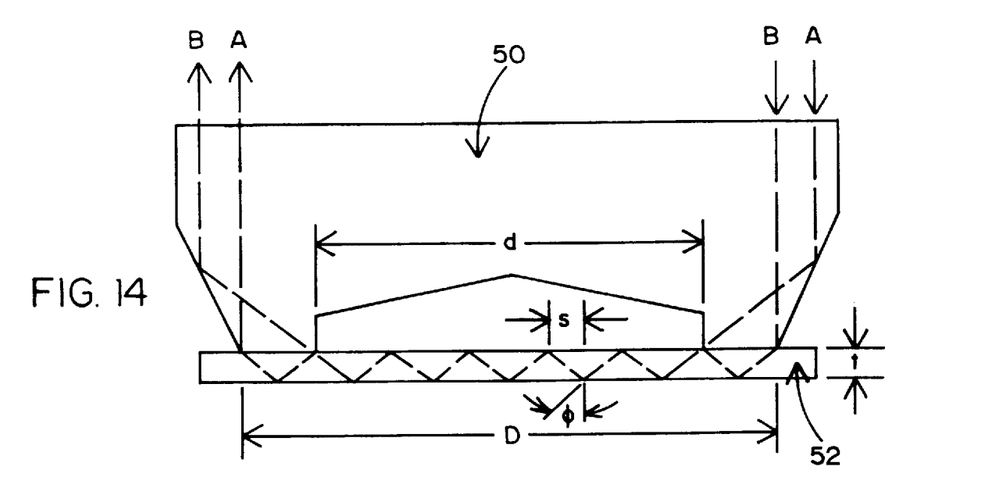
FIG. 14 represents schematically the general case in which the number of reflections at the analyte is designated "n" (not necessarily 2) and the angle of incidence is designated $\phi$ (not necessarily 45 degrees)

FIG. 14 represents a generalized case in which the number of reflections at the sample is chosen to be some number which will be called "n". In addition, let the angle of incidence have some value "$\phi$", which is not necessarily 45 degrees. It can be shown that all of the rays which are parallel to the axis before entering the ATR element will have the same number of reflections (i.e., "n") when the following conditions are met:

$$d=2(n-1)t \tan \phi, \text{ and } D=d(n+1)/(n-1).$$

These equations were derived as follows. First note that in FIG. 14, "s" is used to denote the horizontal distance that a ray travels during one transit across the element 52. From trigonometry:

$$s=t \tan \phi. \tag{1}$$

By inspection, it is seen that the number of reflections that either ray "A" or ray "B" makes with the sample is equal to:

$$n=d/2s+1, \text{ or } d=(n-1)2s \tag{2}$$

and also that:

$$D = d + 4s, \text{ or } D = (n+1)2s \quad (3)$$

Combining these equations results in:

$$d = (n-1)2t \tan \phi \text{ and } D = d(n+1)/(n-1)$$

Figure 8:
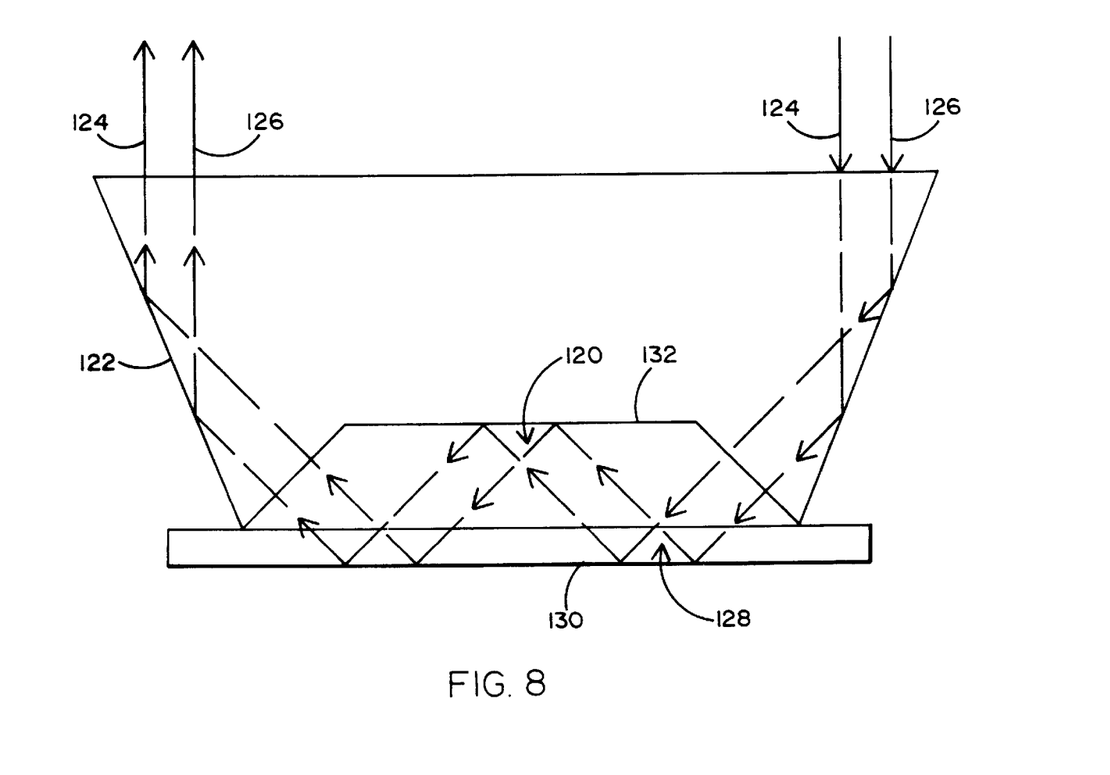
FIG. 8 is a schematic showing another embodiment of the present invention.

FIG. 8 is a schematic showing a different embodiment of the invention. This design uses a much smaller ZnSe element 120, which is trapezoidal in cross section. The paraxial radiation is reflected by a conical metallic mirror 122, rather than by the inside surface of the ZnSe element. After this reflection, each ray enters the ZnSe element at normal incidence, and strikes the interface with the analyte (sample) at the desired angle.

Two rays are represented by dashed lines in FIG. 8, rays 124 and 126. The rays enter parallel to the axis of the probe, are reflected off conical wall 122, passing through the ZnSe element 120 and into the diamond element 128. Each ray is shown reflected twice at the sample contacting surface 130 of element 128. Each entering ray is reflected from surface 130 through both element 128 and element 120, where it is reflected downward by the upper surface 132 of element 120. Because there is no recess provided in the lower surface of element 120, it is necessary that a light blocking element (not shown in FIG. 8) engage the top surface 132 of element 120. After two reflections at the sample surface 130, each ray is reflected by conical wall 122, and exits along a path parallel to the axis of the probe.

Figure 9:
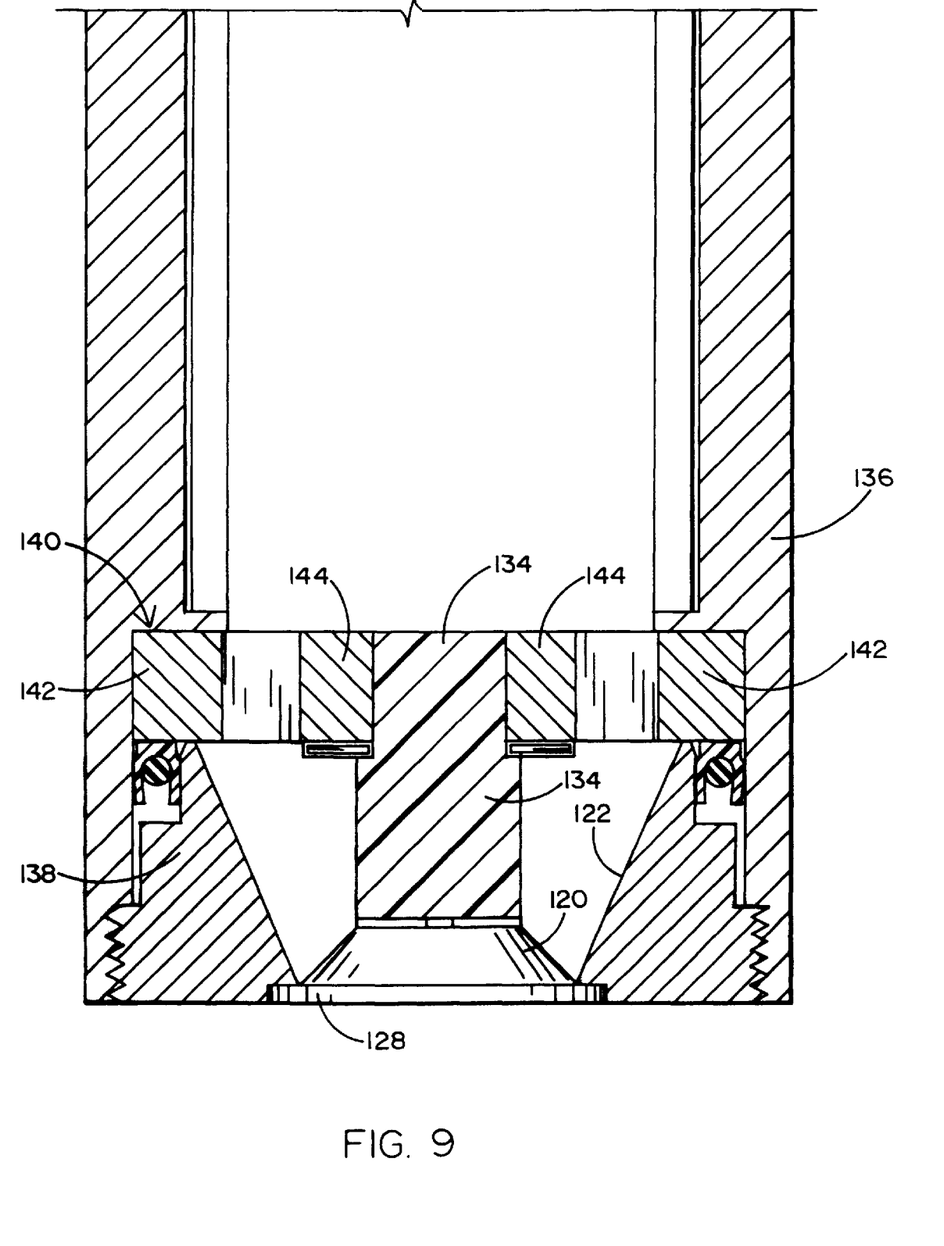
FIG. 9 is a cross-section showing the mechanical design appropriate for the concept of FIG. 8.

FIG. 9 shows a mechanical design appropriate for supporting the device of FIG. 8. Since the only area of the assembly usable for incident and excitant radiation is the area of the metal reflecting cone 122, an optical stop 134 is used to block all other areas. The member 134 which may be made of plastic material, is made rather thick in the axial direction so as to provide support for the other elements of the device. The probe has an outer cylindrical body 136, within which a light guide is mounted. An annular member 138 has threaded engagement with the lower end of body 136; and the inner wall of member 138 provides the conical reflecting surface 122. Diamond window element 128 is mounted in the bottom of the probe assembly as part of the annular member 138; it may be secured in place by brazing or soldering.

The ZnSe element 120 is pressed against the window 128 by means of the light blocking post 134, which is supported by the center area of a spider-like member 140. A compliant (resilient) element, such as a Belleville washer, may be mounted between the spider and the post so as to provide a controllable force. Spider-like body member 140 has an outer annular wall 142, a central annulus 144, and a plurality of arms (not shown) connecting its center to the outer wall.

Figure 15:
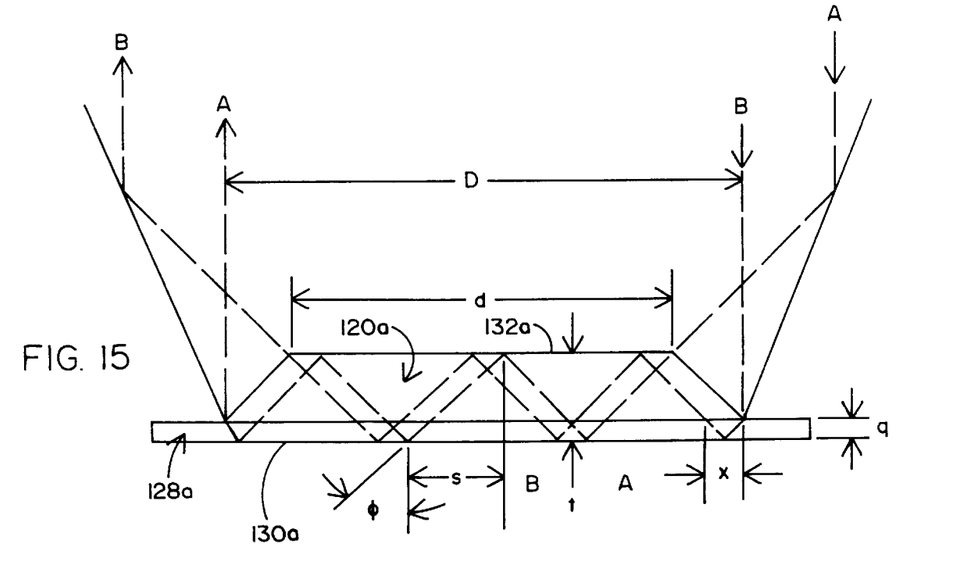
FIG. 15 is a schematic illustrating the dimensions whose relationship is significant in the embodiment of FIG. 8.

For the alternative embodiment of the invention represented by FIG. 8, FIG. 15 shows the critical dimensions which insure that each ray has an equal number of reflections at the sample surface. These dimensions have been adjusted so that the limiting rays "A" and "B" experience the same number of reflections (in this case 3).

In FIG. 15, the rays reflected at the sample travel through both the sample-contacting (diamond) element 128a and the backing (ZnSe) element 120a before being reflected back toward the sample at the upper surface 132a of element 120a. The total linear thickness of elements 128a and 120a is designated by the letter "t", and the thickness of the sample-contacting element 128a is represented by the letter "q". Also, the letter "x" designates the distance in the horizontal plane between the two points at which limiting ray A passes through the upper surface of element 128a before and after it is reflected at sample surface 130a.

The situation in the FIG. 8 embodiment is unlike that in the FIG. 5 embodiment. Limiting rays A and B are not coincident within the elements 128a and 120a, but are separated by the distance "x" as measured in the horizontal plane. The reason is that the metallic reflecting surface 122a necessarily ends at the rear surface of the lower ATR element 128a. This is for two reasons. First, if the element 128a is composed of diamond material, it is not practical to bevel it as is done with the inner element. Second, the diameter of this element needs to be wider than that of the inner element for mounting and sealing purposes.

From trigonometry, it is seen that:

| | |
|---|---|
| | $s = t \tan\phi$ and $x = 2q \tan\phi$ |
| By inspection, | $d = (n - 1)2s + x$ |
| or | $d = [2(n - 1)t + 2q] \tan\phi$ |
| and | $D = 2ns$ or $D = 2nt \tan\phi$ |

This can also be written: $D = ntd/[(n-1)t+q]$ We see from this the importance of keeping the outer element 128a as thin as possible in this design. For example, in the limit of $q=t$, D will be equal to d, and the radial dimension of the entrance aperture will have gone to zero, i.e., no light can enter the ATR.

A comparison of the embodiments of FIGS. 5 and 8 shows that each has certain advantages over the other. Originally, the FIG. 8 embodiment was considered preferable because it minimizes the total path length, both in the diamond and in the ZnSe, and thus has the advantage of minimizing the effects of the inherent low frequency absorption of this material. It also allows the use of an arbitrarily thin diamond element, without decreasing the entrance aperture.

On the other hand, the FIG. 5 embodiment has at least three benefits. First, the use of a relatively thick diamond element 52 makes it possible to apply considerable force in sandwiching the two elements 50 and 52 together. This will assure that optical contact is achieved across the surface even if one or the other element starts out being slightly bowed. In addition, it will make it possible for the probe to withstand considerable pressure from the chemical process being monitored, without bowing the elements. Second, the large diameter, thick diamond element makes it possible to use a compliant seal between the diamond and the body of the probe structure. This eliminates the need to braze the diamond to the probe structure. Brazing is undesirable because it can tend to bow the diamond, and it involves materials which may not be compatible with the corrosive chemicals to be encountered. Third, any reflection from the interface between the diamond 52 and the backing element 50 will not be redirected back parallel to the probe axis, and thus will not constitute stray light.

Figure 10:
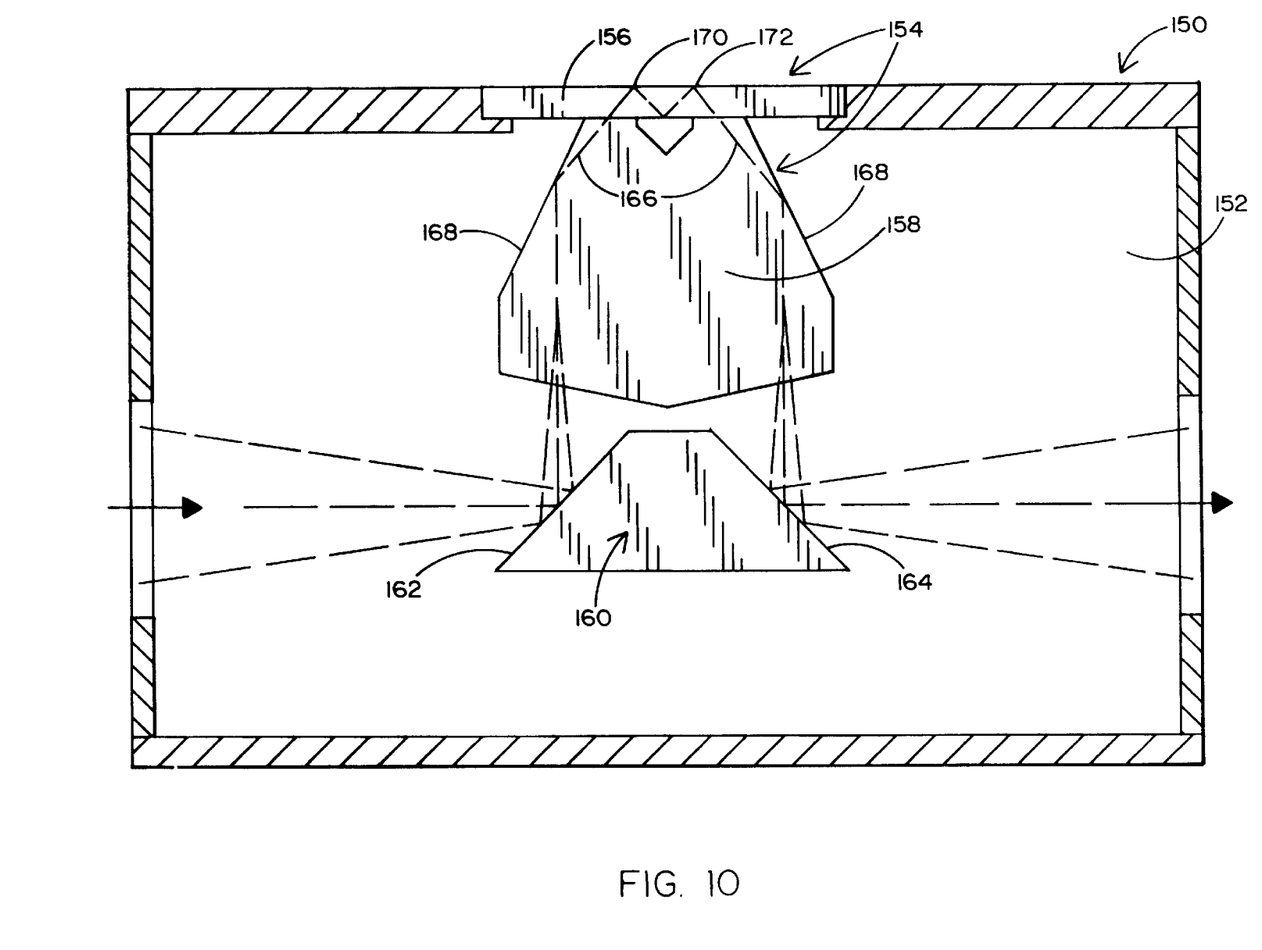
FIG. 10 shows in partial cross-section a structure other than a probe as the mounting structure for a two-layer ATR sensor.

FIG. 10 illustrates a structure in which the horizontal cross-section of the ATR sensing device may be rectangular, rather than round. It also shows a structure which does not involve a probe inserted into the sample. A housing 150 has a chamber 152 containing an ATR sensing head 154 which is engaged by a sample placed on top of the housing. The housing top supports a diamond element 156, which is engaged from above by a sample placed on top of element 156. As in the FIG. 5 embodiment, the inner side of element 156 is engaged by a ZnSe element 158, through which radiation passes on its way to and from the element 156. Radiation is shown entering chamber 152 at the left side and exiting chamber 152 at the right side. A roof-top mirror structure 160 is used to direct radiation to and from the sample. The mirror surfaces 162 and 164 on structure 160 are flat surfaces inclined in such a way that they redirect the radiation at a substantial angle, e.g., 90°. Entering radiation is reflected upwardly, as shown, by the left mirror surface 162, and exiting radiation is reflected laterally by the right mirror surface 164. A ray 166 is shown reflected into diamond element 156 by the conical outer surface 168 of element 158. After ray 166 has been reflected twiice, at points 170 and 172, of the sample-engaging surface of element 156, it is reflected downwardly by conical surface 168.

The FIG. 10 structure is so arranged that a sample, such as a pliable solid material, may be pressed on top of element 156 for spectral analysis.

From the foregoing description, it will be apparent that the apparatus and method disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A sensing apparatus for spectral analysis which is adapted to cause reflection of infrared rays by a sample, comprising:

supporting structure through which entering and exiting rays pass;

radiation-path-determining structure carried by the supporting structure which determines the path of each light ray into reflection at the sample;

said path-determining structure including (a) a sample-contacting element which is infrared transparent and which is resistant to corrosion and (b) a supporting element for the sample-contacting element which is infrared transparent and which presses against the inner surface of the sample-contacting element; and said path-determining structure including a first surface which is a sample-contacting surface, and a second surface, parallel to the first surface, which is a reflecting surface, the dimensions of the second surface being so related to the separation dimension between the first and second surfaces that substantially all rays which are reflected from both the first and second surface at a specified angle have the same number of reflections.

2. The sensing apparatus of claim 1 in which the rays are reflected into the sample-contacting element by a reflecting surface which causes the paths of those rays which are initially parallel to (a) make substantially the same angle with the axis of the radiation-path-determining structure, and (b) meet the sample surface at the desired angle of incidence.

3. The sensing apparatus of claim 2 in which the reflecting surface is conical.

4. The sensing apparatus of claim 1 in which the path-determining structure is so shaped that back reflected incoming rays are deflected from the paraxial direction, in order to minimize stray light in the sensing apparatus.

5. The sensing apparatus of claim 1 in which the supporting element has a centrally-located recess formed in its outer surface which is pressed against the inner surface of the sample-contacting element;

the return reflection surface being the inner surface of the sample-contacting element coextensive with the recess in the supporting element.

6. The sensing apparatus of claim 1 in which the return reflection surface is the inner surface of the supporting element, the rays traveling through both the sample-contacting element and the supporting element before being reflected back toward the sample surface.

7. The sensing apparatus of claim 1 in which the material forming the sample-contacting element is diamond.

8. The sensing apparatus of claim 7 in which the material forming the supporting element is zinc selenide.

9. A sensing apparatus for spectral analysis which is adapted to cause reflection of infrared rays at a sample, comprising:

supporting structure through which entering and exiting rays pass;

a bilayer attenuated total reflectance (ATR) device carried by the supporting structure;

the first layer of the ATR device being formed of chemically resistant material and being in contact with the sample;

the second layer of the ATR device being formed of infrared transparent material and being pressed against the inner surface of the first layer; and ray-directing means associated with the bilayer ATR device causing the rays to enter the first layer on substantially parallel paths, and to be reflected at the sample surface at substantially the same angle of incidence;

said bilayer ATR device including a first surface which is a sample contacting surface, and a second surface, parallel to the first surface, which is a reflecting surface, the dimensions of the second surface being so related to the separation dimension between the first and second surfaces that substantially all rays which are reflected from both the first and the second surfaces at a specified angle have the same number of reflections.

10. The sensing apparatus of claim 9 in which the ray-directing means includes a conical outer surface of the second layer.

11. The sensing apparatus of claim 9 in which the ray-directing means is a conical mirror which reflects rays into the second layer.

12. The sensing apparatus of claim 9 in which the reflecting surface is the inner surface of the first layer.

13. The sensing apparatus of claim 9 in which the reflecting surface is the inner surface of the second layer.

14. The sensing apparatus of claim 9 in which the supporting structure is a probe adapted to be inserted into a sample, and having a tubular radiation path leading to the bilayer ATR device.

15. The sensing apparatus of claim 9 in which the supporting structure is a platform adapted to support a sample.

16. The sensing apparatus of claim 9 in which the inner surface of the second layer, through which rays first enter the ATR device, is a shallow cone which deflects any back reflected incoming rays away from the paraxial direction, in order to minimize stray light in the sensing apparatus.

17. The sensing apparatus of claim 12 in which the ray-confining means has these critical dimensions of the bilayer ATR device: the thickness (t) of the first layer, and the width (d) of the return reflection surface.

18. The sensing apparatus of claim 17 in which the critical dimensions are symmetric with respect to the axial center of the ATR device, and conform to the following relationship:

$$d=2(n-1)t \tan \phi$$

where n represents number of reflections of each ray at the sample, and $\phi$ represents the angle of incidence of such reflections.

19. The sensing apparatus of claim 13 in which the ray-confining means has these critical dimensions of the bilayer ATR device: the combined thickness (t) of the first and second layers, and the width (d) of the return reflection surface.

20. The sensing apparatus of claim 19 in which the critical dimensions are symmetric with respect to the axial center of the ATR device, and conform to the following relationship:

$$d = 2(n-1)t \tan \phi$$

where n represents number of reflections of each ray at the sample, and $\phi$ represents the angle of incidence of such reflections.

\* \* \* \* \*